United States Patent [19]

Segmüller et al.

[11] Patent Number: 5,549,681
[45] Date of Patent: Aug. 27, 1996

[54] ARTICULATED PROSTHESIS

[75] Inventors: Gottfried Segmüller; Gontran Sennwald, both of St. Gallen, Switzerland; Zsuzsa Cserhati, Freyastrasse 21, CH-8004, Zürich, Switzerland; Gerard R. Schaap, Hilversum, Netherlands

[73] Assignee: Zsuzsa Cserhati, Zurich, Switzerland

[21] Appl. No.: 427,410

[22] Filed: Apr. 24, 1995

[30] Foreign Application Priority Data

Apr. 26, 1994 [DE] Germany .......................... 44 14 426.1

[51] Int. Cl.$^6$ ..................................................... A61F 2/30
[52] U.S. Cl. .................. 623/18; 623/19; 623/21; 623/22; 623/23
[58] Field of Search ................................ 623/16, 18, 19, 623/21, 22, 23

[56] References Cited

U.S. PATENT DOCUMENTS

| 4,213,208 | 7/1980 | Marae | 623/21 |
| 4,279,041 | 7/1981 | Buchholz | 623/23 X |
| 4,944,758 | 7/1990 | Bekki et al. | 623/21 |
| 5,147,386 | 9/1992 | Carignan et al. | 623/21 |
| 5,290,314 | 3/1994 | Koch et al. | 623/21 |

*Primary Examiner*—Mary Beth Jones
*Attorney, Agent, or Firm*—Tarolli, Sundheim, Covell, Tummino & Szabo

[57] ABSTRACT

The articulated prosthesis comprises two cooperating prosthesis portions each portion having an anchoring stem to fix the prosthesis portion in a bone. The first prosthesis portion is provided with a essentially ball-shaped head member which comprises two diametrically opposite flattened portions. The second prosthesis portion is provided with a shell member having essentially the shape of a spherical sector and having a height which is greater than the radius of the head member. It is provided with a window allowing the assembling of the first and second prosthesis portions in an assembling position. To assemble the two portions to an articulated prosthesis, the two portions are aligned to each other in the assembling position, the head member is inserted into the shell member and the two portions are rotated with respect to each other into an operating position. In that operating position, the articulated prosthesis may be subjected to a pull strain without the danger of luxation.

18 Claims, 3 Drawing Sheets

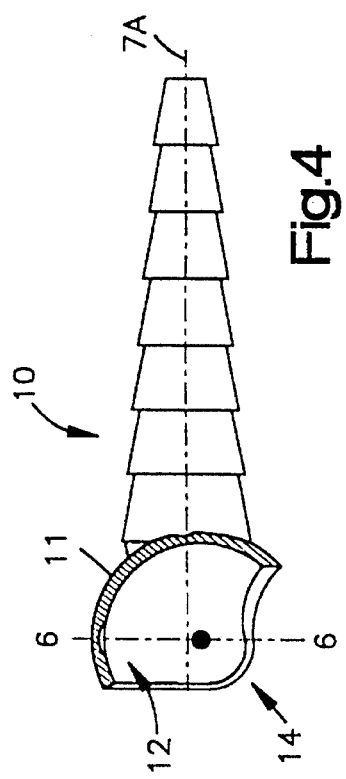
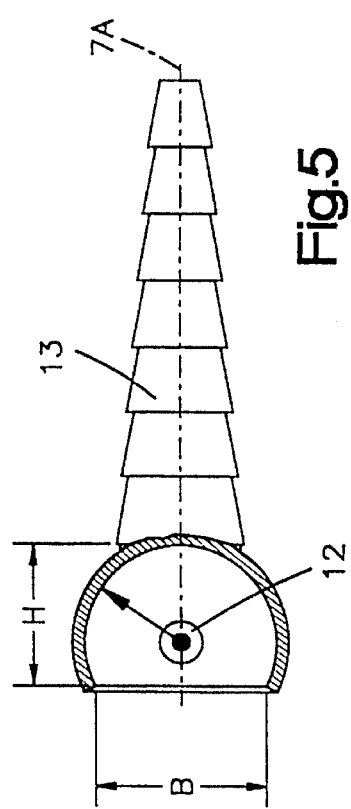
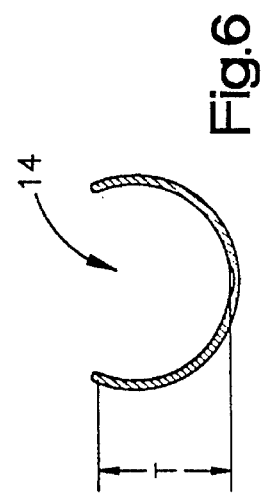
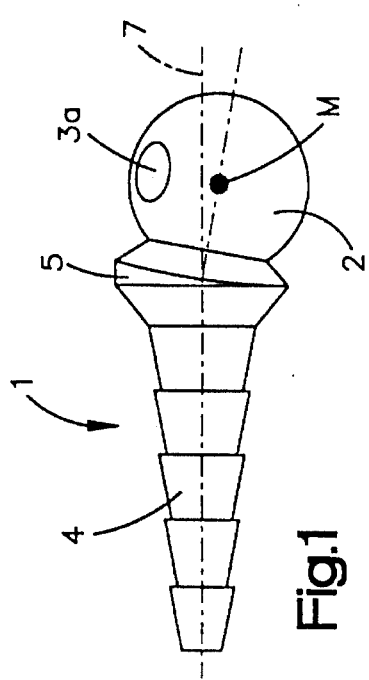
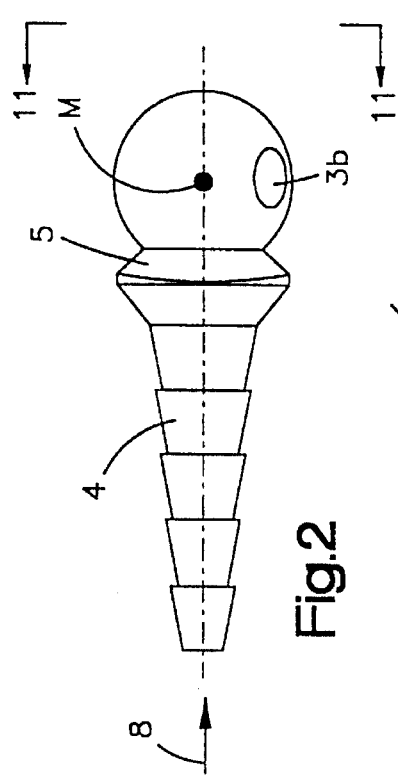
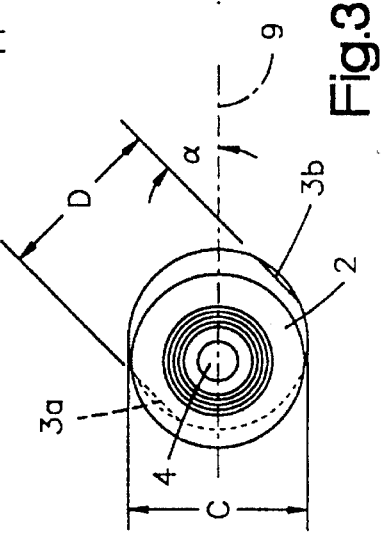

ARTICULATED PROSTHESIS

FIELD OF THE INVENTION

The present invention refers to an articulated prosthesis comprising a first prosthesis portion provided with a first stem member adapted to be anchored in a first bone portion and a second prosthesis portion provided with a second stem member adapted to be anchored in a second bone portion. The articulated prosthesis of the invention is useful in uniting two bone portions to form an articulated joint, such as a finger joint.

PRIOR ART

Known articulated prostheses of this kind are known in the art in various embodiments and variants; usually, they comprise two cooperating prosthesis portions which can be assembled to form a joint. One of the prosthesis portions may be provided with a concave shell member to swiveably support a ball-like element of the other prosthesis portion. In this way, a joint is realized which can reproduce the physiologic movability to a more or less realistic extent. The main disadvantage of these prostheses known in the art is that they cannot be subjected to pull strain, but only to pressure strain. The pulling forces occurring under usual load circumstances have to be compensated for by the muscles and ligaments. A further disadvantage of the known prostheses, particularly of those which comprise bearing surfaces coated with self lubricating plastic material, is that the useful life is quite short since the bearing surfaces are subjected to considerable wear.

In the European Patent Application No. 0,310,483, an articulated prosthesis is disclosed for a finger joint, particularly a metacarpo-phalangial or interphalangial prosthesis which consists of two cooperating prosthesis portions which form the real joint. Both portions are provided each with a stem member adapted to be implanted in a marrow channel. The one portion comprises at one end a housing-like member which is open at one side, while the other portion comprises a head member adapted to be received in the housing of the other portion. The housing is provided at its outer side with two edge portions which serve for supporting two concave recesses of the head member. Moreover, the head member is designed such that it comprises two plane lateral surfaces whose distance is somewhat less than the width of the head member. Thus, the head member and these lateral surfaces, respectively, are guided in such a way in the housing that the two portions are movable mainly in one plane. In a preferred embodiment, it is provided for that the finger joint prosthesis can tolerate a certain lateral movement if it is in its stretched position.

Disadvantageous with such a prosthesis is that it can take only pressure forces and that all pull forces must be taken by the muscles and/or ligaments. Experience, however, has shown that in the case of patients undergoing a finger joint implantation particularly the ligaments cannot show the required stability and elasticity. Thus, there is a great danger that such a finger joint prosthesis dislocates even on quite small pull forces which can occur in daily life. Consequently, it would be highly desirable to have a finger joint prosthesis which itself could take such frequently occurring pull forces. A further disadvantage of this prosthesis is that lateral movements are possible only in the stretched condition thereof whereby no real guiding surfaces are present for a lateral movement.

In the European Patent Application No. 0,280,424, an articulated prosthesis is disclosed for a finger joint. The prosthesis is capable of joining two bones and basically consists of two stems, each having a bearing means integral with one end of the stem which together form a hinged joint pivotal about an axis. Snap on coupling means integral with a hinge pin component is provided on each side of the bearing. Even if such a prosthesis can take certain pull forces, it has the disadvantage that the two prosthesis portions are pivotal with respect to each other only in one plane. Moreover, the design of such a prosthesis is quite complex with the result that it is expensive to manufacture. Finally, it must be mentioned that such a finger joint prosthesis is unnaturally big in the region of the real joint; this can lead to difficulties during the implantation or to subsequent complications.

A further disadvantage of all known articulated prostheses of the kind which are pivotal only in one plane may be seen in the fact that lateral forces acting beyond the plane of motion of the prosthesis can induce great moments and shear forces which strain the prosthesis in an intolerable manner with the result that the prosthesis may be damaged or even destroyed.

OBJECTS OF THE INVENTION

It is an object of the present invention to provide an improved articulated prosthesis of the kind mentioned herein before which itself can be subjected to pressure and to pull forces immediately after implantation thereof.

It is a further object of the present invention to provide an improved articulated prosthesis of the kind mentioned herein before which provides for a greater freedom of movement, particularly in more than one plane.

It is a still further object of the present invention to provide an improved articulated prosthesis of the kind mentioned herein before which ensures that no danger of luxation exists under normal circumstances.

Finally, it is an object of the present invention to provide an improved articulated prosthesis of the kind mentioned herein before which can be easily assembled during implantation to bring the two prosthesis portions into the operating position.

SUMMARY OF THE INVENTION

To meet these and other objects, the present invention provides an articulated prosthesis comprising a first prosthesis portion provided with a first stem member adapted to be anchored in a first bone portion and a second prosthesis portion provided with a second stem member adapted to be anchored in a second bone portion.

The first prosthesis portion comprises an essentially ball-shaped head member which is provided with two diametrically opposite flattened portions, and the second prosthesis portion comprises a shell member having essentially the shape of a spherical sector and being made of one piece; thereby, the shell member is adapted to cooperate with the head member.

The shell member has a height which is greater than the radius of the head member. Thereby, the spherical sector shaped configuration of the shell member is maintained also in that height region which extends beyond the radius of the head member. The shell member is provided with at least one window allowing the assembling of the first and second prosthesis portions to an articulated prosthesis. The width of the window, measured in the region of the front edge of the shell member, is smaller than the diameter of the head member, measured remote from the two flattened portions. Simultaneously, the width of that window, measured in the region of the front edge of the shell member, is greater than the distance between the two flattened portions of the head member.

Thus, the basic principle of the prosthesis of the invention is based on the fact that the two prosthesis portions are designed such that they can be assembled to form the real prosthesis when they are in a first position, i.e. in an assembling or mounting position, and then can be rotated against each other from that assembling or mounting position into an operating position in which the articulated prosthesis may be subjected not only to pressure forces, but also to pull forces. For this purpose, the head member of the first prosthesis portion is provided with flattened portions, while the other prosthesis portion comprises one or two windows in its spherical sector-shaped shell member, —whose height is greater than the radius of the ball-shaped head member—, by means of which the head member can be inserted into the shell member if the two prosthesis portions are in the assembling or mounting position. Thereafter, the two portions are rotated against each other to bring them into the operating position in which the so formed articulated joint is capable of taking also pull forces.

According to a preferred embodiment, the first and second prosthesis portions, when they are in their operating position, are rotated against each other by an angle of between 10° and 80° as compared to the assembling position. The angle by which one prosthesis portion is rotated with respect to the other prosthesis portion once the prosthesis portions have been assembled in the assembling position is chosen such that it is greater than the physiology of the particular joint normally would allow. Thus, the angle of rotation to bring the prosthesis portions from the assembling position to the operating position can be adapted to the particular physiological prerequisites, depending on the kind of joint to be replaced by the prosthesis, and can be taken into account when the articulated prosthesis is manufactured. In this way, it is ensured that the articulated prosthesis of the invention is not dislocated under normal use of the joint. For example, the afore mentioned angle of rotation can be made relatively small in the case of a forefinger joint, but considerably greater in the case of a shoulder joint.

According to a further embodiment, the center of the head member of the first prosthesis portion is offset with respect to the central longitudinal axis of the first stem member. Particularly, the head member may be inclined with respect to the central longitudinal axis of the first stem member. In this way, it is made possible that the first prosthesis portion may be more swiveled in a particular direction than this would be the case with a symmetrically fixed head member.

According to a still further embodiment, the essentially spherical sector shaped shell member of the second prosthesis portion is provided with a recess adapted to receive a lubrication fluid. Thus, a reliable lubrication of the bearing surfaces is ensured. The lubrication may be further improved if the bearing surface of the ball shaped head member of the first prosthesis portion is provided with a plurality of recesses.

BRIEF DESCRIPTION OF THE DRAWINGS

In the following, there will be described an embodiment of the articulated prosthesis according to the invention, with refernce to the accompanying drawings, in which:

FIG. 1 shows a first lateral view of the first prosthesis portion which comprises an essentially ball-shaped head member;

FIG. 2 shows a second lateral view of the first prosthesis portion shown in FIG. 1, but rotated by 90° around its longitudinal axis;

FIG. 3 shows a front view of the first prosthesis portion shown in FIGS. 1 and 2 in the direction of arrow 8 in FIG. 2;

FIG. 4 shows a partially sectioned first lateral view of the second prosthesis portion which comprises a shell member essentially in the shape of a spherical sector;

FIG. 5 shows a partially sectioned second lateral view of the second prosthesis portion shown in FIG. 4, but rotated by 90° around its longitudinal axis;

FIG. 6 shows a cross sectional view of the shell member of the second prosthesis portion;

DETAILED DESCRIPTION OF THE PREFERRED EMBODIMENT

Figure 7:
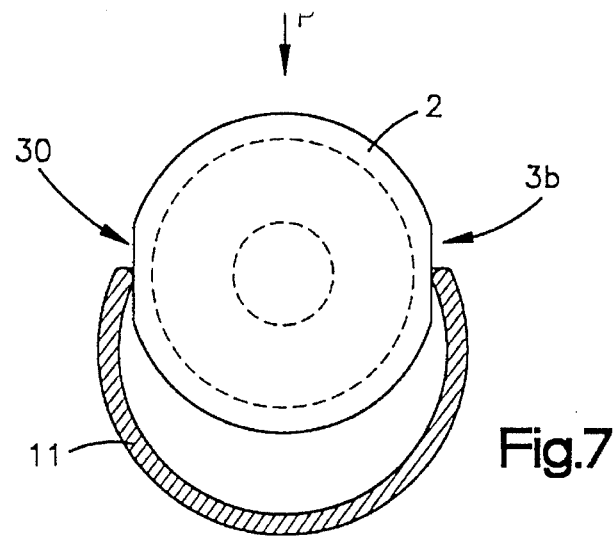
FIG. 7 shows a first schematic illustration of the essential parts of the prosthesis for the explanation of its operation.

In FIGS. 1 and 2, the first one of the two prosthesis portions 1 and 10, respectively, is shown in each case in a lateral view, whereby the first prosthesis portion 1 shown in FIG. 2 is rotated by 90° around its longitudinal central axis as compared to the view of FIG. 1. As can be seen in the drawings, the first prosthesis portion 1 comprises a head member 2 having essentially the shape of a ball as well as a stem member 4 rigidly connected to the head member 2. The stem member 4 serves for anchoring the prosthesis portion 1 in a bone portion; it has an essentially conical shape and is provided with a plurality of indentations.

The head member 2 comprises two flattened portions 3a and 3b which are located diametrically opposite each other. As can be seen in FIG. 1, the center M of the head member 2 is not located on the central longitudinal axis 7 of the stem member 4; in fact, the center M of the head member 2 is somewhat offset to the central longitudinal axis 7. Moreover, the head member 2 is fixed to the stem member 4 by means of an asymmetric adapter member 5 inserted between the head member 2 and the stem member 4; due to the asymmetry of the adapter member 5, the head member 2 is inclined with respect to the central longitudinal axis 7 and, thereby, with respect to the stem member 4 in a particular plane.

In FIG. 3, the first prosthesis portion 1 is shown in an end view from the stem member 4 side, as illustrated by arrow 8 in FIG. 2. It can be clearly seen in the illustration of FIG. 3 that the two flattened portions 3a and 3b, respectively, are located at the head member 2 such that they enclose an angle α of about 45° with the central longitudinal plane 9 common to the head member 2 and the stem member 4. In the operational position of the articulated prosthesis, which will be further discussed herein after, the above mentioned central longitudinal plane 9 coincides with the main articulation plane of the articulated prosthesis.

Figure 11:
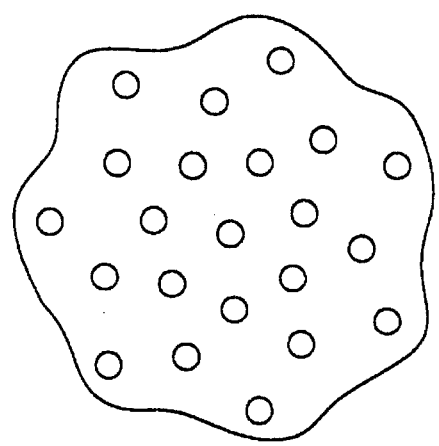
FIG. 11 shows an enlarged schematic illstration of thr surface of the ball-shaped head member of the first prosthesis portion taken along line 11—11 in FIG. 2.

The surface of the head member 2 is provided with a plurality of microscopically small recesses, shown schematically in FIG. 11 which support the lubrication of the two prosthesis portions 1 and 10. Experience has shown that very good results can be obtained if a plurality of such recesses has a diameter of between 1 and 5 μm and a depth of between 1 and 5 μm.

In FIGS. 4 and 5, the second prosthesis portion 10 is shown in a partially sectioned lateral view. This second prosthesis portion 10 comprises a shell member 11 which is made of one piece and generally has the shape of a spherical sector, as well as a stem member 13. The shell member 11 is rigidly connected to the stem member 13. In FIG. 4, the shell member 11 is shown in a first longitudinal sectional view, and in FIG. 5, the shell member 11 is shown in a second longitudinal sectional view in which it is rotated by 90° around the central longitudinal axis 7A of the stem member 13; FIG. 6, finally, shows a cross sectional view of the shell member 11 taken along the line 6—6 in FIG. 4. The inner surface of the shell member 11 corresponds in shape and size to the outer surface of the head member 2 of the first prosthesis portion 1 such that the latter can be swivelingly received therein. As can be clearly seen in FIG. 5, the height H of the shell member 11 is greater than the radius R of the ball-shaped head member 2. Thereby, the spherical sector shaped configuration of the shell member 11 is maintained also in that height region which extends beyond the radius R of the head member 2. Thus, the shell member 11 encloses the head member 2 beyond its head center M once the two prosthesis portions 1 and 11, respectively, have been operatively connected to each other In order to enable the head member 2 of the first prosthesis portion 1 to be inserted into the shell member 11 of the second prosthesis member 10, the shell member 11 is provided on its one side with a window 14 which is dimensioned such that the remaining depth T of the shell member 11 (see FIG. 6) between the front edge thereof and the center of the shell member 11, is greater than the radius R.

The width B of the window 14 in the region of the front edge of the shell member 11 is less than the diameter C of the head member 2 of the first prosthesis portion 1, but more than the distance D between the two flattened portions 3a and 3b, respectively, of the head member 2 (see FIG. 3). The inner surface of the shell member 11, moreover, is provided with a recess 12 which serves for receiving lubrication fluid and thus supports the friction free operation of the prosthesis by feeding lubrication fluid to the articulation surfaces.

The two prosthesis portions 1 and 10, respectively, are preferably made of titanium or a titanium alloy. In the region of the bearing surfaces, the prosthesis portions can be refined by means of ceramic materials, e.g. titanium-niobium- and/or titanium-zirconium-ceramic materials; this measure leads to a very high surface hardness having a Vickers hardness number (measured in $N/mm^2$) of more than 5000, preferably more than 2000, and most preferably in the region of 25000. The advantage of such high surface hardness removes the need to coat the surface of the bearing surfaces with self-lubricating materials and renders possible that the lubrication of the bearing surfaces can be ensured by the natural human articulation fluid which is available anyway. Moreover, such high hardness guarantees that no measurable wear takes place, even after prolonged use of the prosthesis over a period of many years.

The anchoring stem members 4 and 13, respectively, of the two prosthesis portions 1 and 10, respectively, may be coated by hydroxyl apatite, particularly hydroxyl apatite ceramic material; this measure supports the natural growth of the bone material around the stem members 4 and 13, respectively. The stem member 13 of the second prosthesis portion 10 is longer and has a greater diameter than the stem member 4 of the first prosthesis portion 1. Thus, the first prosthesis portion 1 is preferably used for distal implantation, while the second prosthesis portion 10 is used for proximal implantation. Stem members of the kind used in connection with an articulated prosthesis according to the invention are known per se in the art; thus, it is not necessary to further discuss the exact design thereof at this point.

In the following, the principle of use and operation of the articulated prosthesis according to the invention and as described herein before will be further explained, with reference to FIGS. 7 to 9. For simplicity's sake, the two prosthesis portions 1 and 10, respectively, are shown in those figures only with their essential parts. The two anchoring stem members 4 and 13, respectively, are shown schematically in broken lines.

In FIG. 7, the shell member 11 of the second prosthesis portion 10 is shown in a cross sectional view and the head member 2 of the first prosthesis member 1 is shown in a plain view seen from the stem member. In FIGS. 8 and 9, the shell member 11 is shown in a longitudinal sectional view and the head member 2 in a lateral view, whereby the prosthesis portion 1 provided with the head member 2 is shown in FIG. 9 in a position in which it is rotated by 90° around its longitudinal central axis, as compared to the view shown in FIG. 8.

Figure 8:
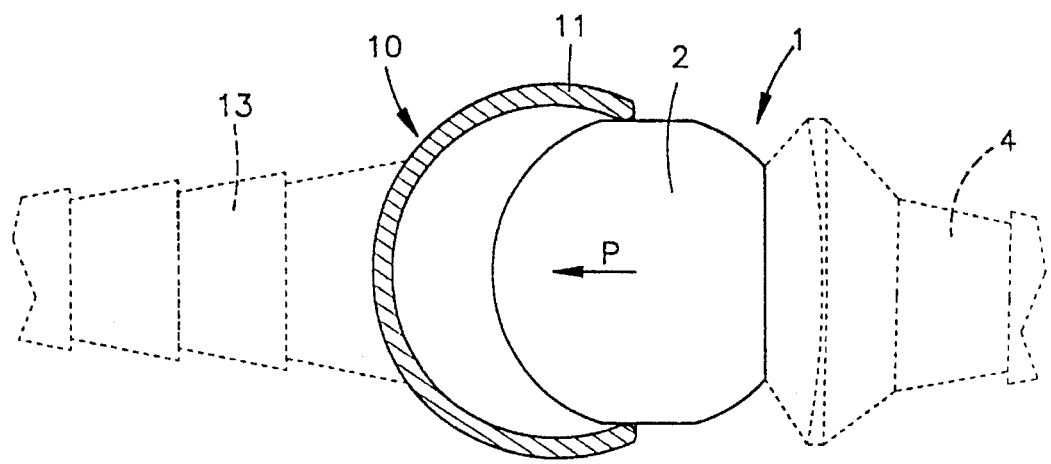
FIG. 8 shows a second schematic illustration of the essential parts of the prosthesis for the explanation of its operation.

In order to insert the head member 2 of the first prosthesis portion 1 into the shell member 11 of the second prosthesis portion 10, the two prosthesis portions 1 and 10, respectively, have to be brought into a mounting position which is shown in FIGS. 7 and 8 in two different views. For this purpose, the flattened portions 3a and 3b, respectively, as shown in FIG. 7, are vertically aligned such that they are directed towards the region of the shell member 11 which extends over the center thereof. In this mounting position, it is possible to assemble the two prosthesis portions 1 and 10, respectively, to an articulated prosthesis, and to separate them from each other. The bearing surface of the shell member 11 simultaneously serves as a stop for the head member of the first prosthesis portion 1 upon assembling the two prosthesis portions.

Figure 9:
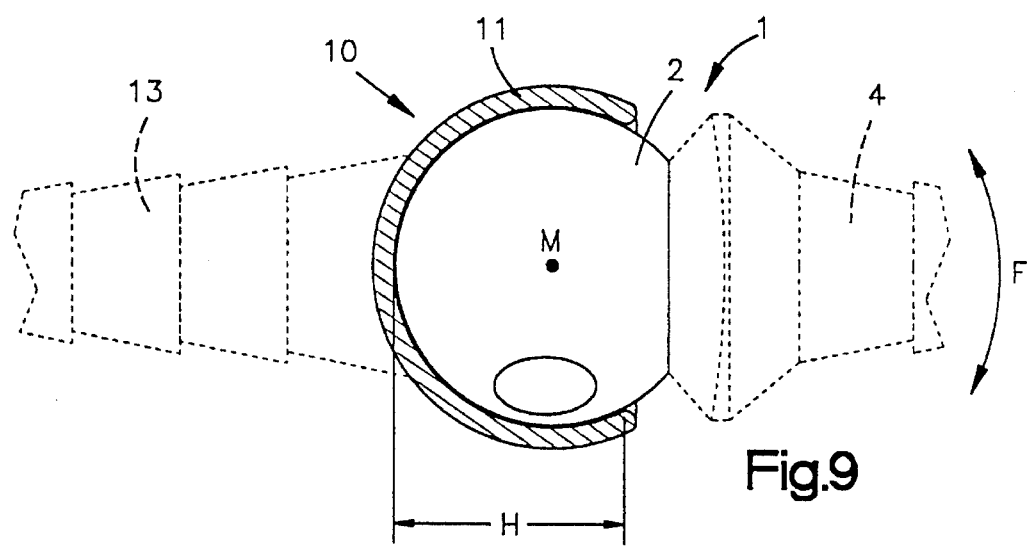
FIG. 9 shows a third schematic illustration of the essential parts of the prosthesis for the explanation of its operation.

In FIG. 9, the articulated prosthesis is shown in an assembled state in its operative position. In this figure, it can be clearly seen that the shell member 11 encloses the head member 2 over more than one half of its surface, i.e. beyond its center M. In order to put the articulated prosthesis into this operating position, the first prosthesis portion 1, after having been inserted into the shell member 11 of the second prosthesis portion 10 as shown in FIGS. 7 and 8 and illustrated by the arrow P, has been rotated by 45°; the result is that the head member 2 and, thereby, the first prosthesis portion 1 is swivelingly received in the shell member 11 of the second prosthesis portion 10 and is surrounded by the shell member 11 beyond its central point M. In this position, the central longitudinal plane 9 of the first prosthesis portion 1 coincides with the main articulation plane of the articulated prosthesis. Thus, the one prosthesis portion can be moved with respect to the other one within certain operational limits and, simultaneously, can be put under pull strain without the danger of luxation.

Upon swiveling the first prosthesis portion 1 with respect to the second prosthesis portion 10, the edges of the shell member 11 of the latter one simultaneously serve as stop means for the first prosthesis portion 1. The only criteria as far as pull strain is concerned is that the two prosthesis portions 1 and 10, respectively, are not allowed to be rotated with respect to each other by an angle of 45°and 135°, respectively, as compared to the assembling or mounting position. As long as this condition is observed, any danger of luxation is avoided. Usually or in most of the cases, such a rotation is impossible due to the physiology of the human body. The angle of possible swing of the first prosthesis portion 1 with respect to the second prosthesis portion 10 in a particular plane is illustrated in FIG. 9 by an arrow F.

The value of 45° of the angle α which is enclosed by the two flattened portions 3a and 3b, respectively, located at the head member 2 with the central longitudinal plane 9 common to the head member 2 and the stem member 4 is not mandatory; this angle can have a value of between 10° and 80° as appropriate, depending on the place in which the articulated prosthesis is implanted.

In the following, the implantation of the articulated prosthesis according to the invention in the human body will be further described. As an example, it is assumed that the articulated prosthesis is designed as an artificial finger base joint.

Generally, each of the two prosthesis portions 1 and 10, respectively, have to be inserted into a bone portion facing the joint to be replaced, and the two prosthesis portions have to be assembled. In the present example, the prosthesis portion 10 which is provided with the shell member 11 is proximally inserted into the metacarpus and the prosthesis portion 1 which is provided with the head member 2 is distally inserted into the phalanx I in a manner known per se in the art. The insertion of these two prosthesis portions 1 and 10, respectively, is effected in a position in which they are aligned with their operating position, as shown in FIG. 9. It is understood that the two prosthesis portions 1 and 10, respectively, are not yet assembled in this phase.

Thereafter, the prosthesis portion 1 inserted into the phalanx I is rotated, together with the associated finger, by such an amount until the two prosthesis portions 1 and 10, respectively, are in their mounting or assembling positions. In the present example, the finger must be rotated by 45° around its longitudinal axis. Now, it is possible to join the two prosthesis portions 1 and 10, respectively, by inserting the head member 2 of the one prosthesis portion 1 into the shell member 2 of the other prosthesis portion 10. Thereafter, the finger and therewith the prosthesis portion 1 inserted into the phalanx I is rotated back into its initial position with the result that the articulated prosthesis takes its operating position and is, theoretically, fully functional. Finally, the tendons, ligaments and muscles can be brought into their proper position and fixed in a manner known per se in the art.

As soon as the bones have taken the assigned stem portions of the articulated prosthesis, the latter one can be fully loaded. The danger of luxation can be practically excluded because this can happen only if the finger is rotated by exactly 45° (according to the present example) and simultaneously strained by a pulling force.

The lubrication of the articulated prosthesis according to the invention is performed by means of the natural articulation fluid. The recess 12 provided in the shell member 11 takes care of such lubrication by serving as a reservoir for the natural lubrication fluid.

Due to the extreme hardness of the movable parts of the articulated prosthesis, no measurable wear of the prosthesis could be observed.

Figure 10:
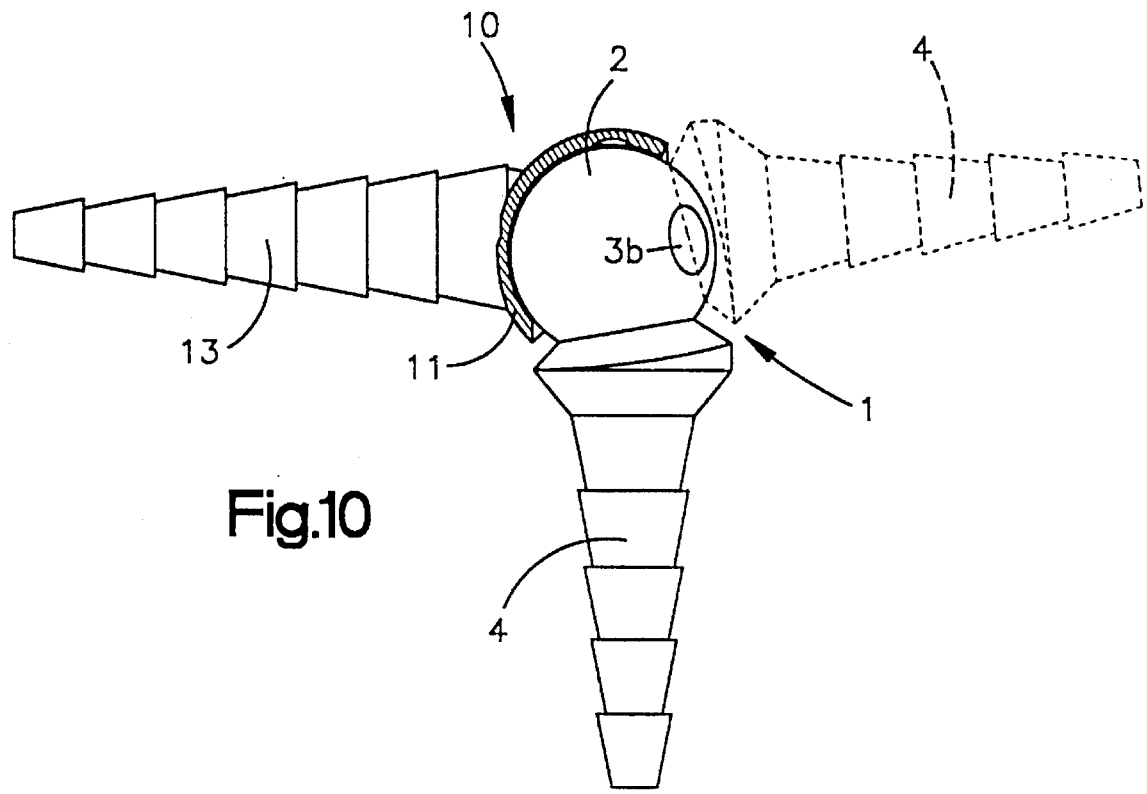
FIG. 10 shows a schematic, partially sectioned lateral view of the articulated prosthesis in which the two portions of the prosthesis are joined together.

FIG. 10, finally, shows a lateral view of the assembled articulated prosthesis according to the invention, with a sectional view of the shell member 11. The maximum amount of movement in the main articulation plane is illustrated by the first prosthesis portion 1 being shown in a first extreme position in solid lines and a second extreme position in broken lines. As can be clearly seen in this drawing figure, the fact that the head member 2 is obliquely fixed to the stem member 4 under a certain angle, as explained herein before with reference to FIG. 1, brings the advantage that the first prosthesis portion 1 can be bent in one direction, in the present example downwards, more than it would be the case of a symmetrically or centrally fixed head member 2. The edges of the shell member 11 of the second prosthesis portion 10 thereby serve as stop means for the bending of the first prosthesis portion 1.

It should be pointed out that the articulated prosthesis illustrated in the drawings and described herein before is only one of many possible embodiments. In other embodiments of the invention, the degree of the offset of the flattened portions 3a, 3b, the height of the shell member 11, the size of the flattened portions 3a, 3b, the maximum swiveling angle of the one prosthesis portion with respect to the other one as well as the kind of implantation, distally and proximally, can be varied within the limits of the scope of the appended claims. It is moreover possible to provide two windows opposite to each other in the shell member 11 instead of one single window 14. Finally, it is understood that the materials of the prosthesis and of the coating can be varied as appropriate, whereby it should be noted that the above possibilities of further embodiments is not final at all.

What is claimed is:

1. An articulated prosthesis comprising:

a first prosthesis portion provided with a first stem member having a central longitudinal axis and adapted to be anchored in a first bone portion;

a second prosthesis portion provided with a second stem member having a central longitudinal axis and adapted to be anchored in a second bone portion;

said first prosthesis portion comprising an essentially ball-shaped head member which is provided with two diametrically opposite flattened portions;

said second prosthesis portion comprising a shell member having essentially the shape of a spherical sector and being made of one piece, said shell member being adapted to cooperate with said head member;

said shell member having a height which is greater than the radius of said head member, the spherical sector shaped configuration of the shell member being maintained also in that height region which extends beyond the radius of said head member;

said shell member being provided with at least one window allowing the assembling of said first and second prosthesis portions to an articulated prosthesis when said first and second prosthesis portions are in an assembling position;

the width of said at least one window, measured in the region of the front edge of said shell member, being smaller than the diameter of said head member, measured remote from said two flattened portions, and the width of said at least one window, measured in the region of the front edge of said shell member, being greater than the distance between said two flattened portions of said head member;

said two portions of said articulated prosthesis, being in its assembled condition, being rotatable against each other from said assembling position to an operating position in which said articulated prosthesis may be subjected to pull strain.

2. An articulated prosthesis according to claim 1 in which said at least one window of said shell member of said second prosthesis portion comprises a single window adapted to allow the insertion of said head member of said first prosthesis portion into said shell member.

3. An articulated prosthesis according to claim 1 in which said first and second prosthesis portions in said operating position are rotated against each other by an angle of between 10° and 80° as compared to said assembling position.

4. An articulated prosthesis according to claim 1 in which said articulated prosthesis has three degrees of freedom when it is in its assembled position, namely two translative degrees of freedom and a rotative degree of freedom.

5. An articulated prosthesis according to claim 1 in which the center of said head member of said first prosthesis portion is offset with respect to said central longitudinal axis of said first stem member.

6. An articulated prosthesis according to claim 5 in which said head member of said first prosthesis portion is inclined with respect to said central longitudinal axis of said first stem member and fixed to said first stem member by means of an asymmetric adapter member.

7. An articulated prosthesis according to claim 1 in which the center of said head member and said central longitudinal axis of said stem member are located in a common central longitudinal plane, said flattened portions provided on said head member of said first prosthesis portion including an angle of between 10° to 80°, with said central longitudinal plane.

8. An articulated prosthesis according to claim 7 in which said central longitudinal plane coincides with the main articulation plane of the articulated prosthesis when said first and second prosthesis portions are in their operating position.

9. An articulated prosthesis according to claim 1 in which the edges of said shell member of the second prosthesis portion are designed as stop members for the first prosthesis portion, thereby limiting the degree of articulation of said first prosthesis portion with respect to said second prosthesis portion.

10. An articulated prosthesis according to claim 1 in which said first stem member of said first prosthesis portion provided with said head member is adapted to be distally anchored in a first bone portion, and said second stem member of said second prosthesis portion provided with said shell member is adapted to be proximally anchored in a second bone portion.

11. An articulated prosthesis according to claim 1 in which said essentially spherical sector shaped shell member of said second prosthesis portion is provided with a recess means adapted to receive a lubrication fluid.

12. An articulated prosthesis according to claim 1 in which said essentially spherical sector shaped shell member of said second prosthesis portion as well as said essentially ball shaped member of said first prosthesis portion are essentially made of titanium or a titanium alloy, whereby at least the inner surface of said shell member and the outer surface of said head member have a Vickers hardness of more than 5000.

13. An articulated prosthesis according to claim 12 in which said first and second prosthesis portion are refined with a ceramic alloy at least in the region of their bearing surfaces.

14. An articulated prosthesis according to claim 1 in which the bearing surface of said ball shaped head member of said first prosthesis portion is provided with a plurality of recesses adapted to support the lubrication of the articulated prosthesis, a plurality of said recesses having a diameter of between 1 µm and 5 µm and a depth of between 1 µm and 5 µm.

15. An articulated prosthesis according to claim 1 in which said first and second stem members are coated with a layer means which supports bone growth, preferably with hydroxyl apatite or hydroxyl apatite ceramic material.

16. An articulated prosthesis according to claim 1 in which the center of said head member and said central longitudinal axis of said stem member are located in a common central longitudinal plane, said flattened portions provided on said head member of said first prosthesis portion including an angle of between 30° and 60° with said central longitudinal plane.

17. An articulated prosthesis according to claim 12 in which the Vickers hardness is more than 20000.

18. An articulated prosthesis according to claim 12 in which the Vickers hardness is in the region of 25000.

* * * * *